(12) United States Patent
Burd et al.

(10) Patent No.: US 8,002,831 B2
(45) Date of Patent: Aug. 23, 2011

(54) MODULAR LATERAL EXPANSION DEVICE

(75) Inventors: Timothy A. Burd, Omaha, NE (US);
Mahmoud F. Abdelgany, Rockaway, NY (US)

(73) Assignee: Custom Spine, Inc., Parsippany, NJ (US)

( * ) Notice: Subject to any disclaimer, the term of this patent is extended or adjusted under 35 U.S.C. 154(b) by 908 days.

(21) Appl. No.: 11/952,352

(22) Filed: Dec. 7, 2007

(65) Prior Publication Data
US 2009/0149957 A1 Jun. 11, 2009

(51) Int. Cl.
*A61F 2/44* (2006.01)
*A61B 17/58* (2006.01)

(52) U.S. Cl. .................. 623/17.11; 623/17.16
(58) Field of Classification Search ..... 623/17.11–17.16
See application file for complete search history.

(56) References Cited

U.S. PATENT DOCUMENTS

| 6,554,863 | B2 | 4/2003 | Paul et al. | |
| 2002/0029084 | A1* | 3/2002 | Paul et al. | 623/23.63 |
| 2005/0187629 | A1* | 8/2005 | Michelson | 623/17.11 |
| 2008/0281346 | A1* | 11/2008 | Greenhalgh et al. | 606/191 |

* cited by examiner

Primary Examiner — Thomas C. Barrett
Assistant Examiner — Michael T Schaper
(74) Attorney, Agent, or Firm — Rahman LLC (57) ABSTRACT

A modular lateral expansion device to be inserted into a vertebral body. The modular lateral expansion device comprises a pair of complementary lateral members. Each of the lateral members includes a first end, a second end, a first lateral portion, a second lateral portion, a top wall, a bottom wall, and a cavity configured through the top wall and the bottom wall. The top wall includes a top ridge and a top contour surface and the bottom wall includes a bottom ridge and a bottom contour surface. The top ridge and the bottom ridge are inwardly angled into the second lateral portion. The first lateral portion includes a plurality of cuts. The second lateral portion includes a first slot positioned at an edge of the second lateral portion and a second slot positioned in a substantially central area of the second lateral portion.

19 Claims, 9 Drawing Sheets

MODULAR LATERAL EXPANSION DEVICE

BACKGROUND

1. Technical Field

The embodiments herein generally relate to medical devices, and, more particularly, to a modular lateral expansion device used during orthopedic surgeries.

2. Description of the Related Art

In lumbar interbody spinal fusion procedures, two adjacent vertebral bodies are fused together by entirely or partially removing the degenerated intervertebral disc between two adjacent vertebrae and inserting an implant within the vertebral body. Lastly, fusion material (e.g., bone graft) may be placed within the vertebral body which along with the body's natural cells promotes bone formation.

The greatest compressive strength in the spine lies within the outer 30% of the vertebral bodies. Due to variable soft tissue anatomy, it is often difficult surgically to seat intervertebral body devices sufficiently laterally to capture and utilize this portion of bone. Thus, poor placement and subsidence of implants can occur leading to implant failure and diseases of the spine such as kyphosis (e.g., a curvature of the upper spine which can be either the result of bad posture or a structural anomaly in the spine), lordosis (e.g., an inward curvature of a portion of the vertebral column) and foraminal stenosis (e.g., narrowing of vertebral foramen). Implant failure can and does lead to catastrophic clinical failure and exceedingly difficult and potentially dangerous spinal revision strategies.

Conventional implants may use one-piece devices to fill the interbody space. The size of the space filled is dictated by multiple factors such as the surrounding soft tissues (e.g., great vessels, ureter, bowel, sympathetic nerves, etc.), aggressiveness of the surgeon performing the surgery, and the type of implant chosen. These implants usually do not violate the vertebral endplate but do not reliably reach the outermost structurally significant area of bone. The devices are routinely placed centrally within the interbody space where they are commonly in contact only with the softest portion of bone, not the more structurally sound outer cortical apophyseal bone.

Various insertable implants are available in different shapes and configurations. An example of such insertable implants is an expandable cage, which often has treads, which are teeth of spikes that engage the vertebral endplates. Usually, these cages can be screwed or inserted into the interbody via distraction tools only in the cephalocaudal direction (e.g., anteroposterior direction). Cages also require destruction of the vertebral endplate by tapping or cutting the structural bone, thus leading to a greater rate on implant subsidence and foraminal stenosis. Accordingly, there remains a need for a new modular lateral expansion device for placing between vertebral bodies within the vertebral body both in lateral and cephalocaudal directions for enhanced structural support of the spine.

SUMMARY

In view of the foregoing, an embodiment herein provides a modular lateral expansion device to be inserted into a vertebral body, the modular lateral expansion device comprising a pair of complementary lateral members. Each lateral member includes a first end, a second end positioned opposite to the first end, a first lateral portion, a second lateral portion, a top wall, and a bottom wall. The first lateral portion and the second lateral portion are positioned opposite to each other and are attached to each of the first end and the second end. The top wall and the bottom wall are attached to each of the first end, the second end, the first lateral portion, and the second lateral portion. The bottom wall is positioned opposite to the top wall.

The second end further includes a hole. The first lateral portion further includes a plurality of cuts. The second lateral portion further includes a first slot positioned at an edge of the second lateral portion and a second slot positioned in a substantially central area of the second lateral portion. The top wall includes a top ridge and a top contour surface and the bottom wall further includes a bottom ridge and a bottom contour surface. The top ridge and the bottom ridge are inwardly angled into the second lateral portion and flank the second slot. The lateral member further includes a cavity configured through the top wall and the bottom wall. The cavity further includes a plurality of ribs. The plurality of ribs may be positioned parallel to each other and may be adapted to provide structural integrity to the lateral member.

The lateral member may further comprise a plurality of holes, a plurality of pins and a concave edge positioned opposite to the first slot. The plurality of holes and the plurality of pins are positioned on the second lateral portion such that each hole may be positioned on opposite diagonal corners of the second lateral portion, and each pin may be positioned on opposite diagonal corners of the second lateral portion. The plurality of pins may be composed of materials capable of detection by x-ray imaging. The materials may include any of titanium and tantalum. The concave edge may be adapted to form a funnel when aligned with a concave edge of a complementary lateral member. The first slot and the second slot may be dimensioned and configured to permit medial bone growth on the lateral member, and the plurality of cuts may be dimensioned and configured to permit lateral bone growth in the lateral member. The top ridge and the bottom ridge may be positioned opposite to each other and adapted to provide torsional stability for posterior lumbar interbody fusion (PLIF) insertion of the lateral member into a vertebral body.

In another aspect, an apparatus to structurally support a vertebral body comprises a pair of lateral members. Each of the lateral members includes a first end, a second end, a first lateral portion, a second lateral portion, a top wall, and a bottom wall. The first end includes a curved configuration and the second end includes a substantially straight configuration. The second end is positioned opposite to the first end. The first lateral portion and the second lateral portion are attached to each of the first end and the second end. The second lateral portion is positioned opposite to the first lateral portion. The top wall and the bottom wall are attached to each of the first end, the second end, and pair of lateral portions. The bottom wall is positioned opposite to the top wall.

The second end further comprises a hole dimensioned and configured to permit insertion means to grip and remove the apparatus into the vertebral body. The first lateral portion includes a plurality of cuts. The second lateral portion includes a first slot positioned at an edge of the second lateral portion and a second slot positioned in a substantially central area of the second lateral portion. The top wall includes a top ridge and a top contour surface and the bottom wall includes a bottom ridge and a bottom contour surface. The top ridge and the bottom ridge are inwardly angled into the second lateral portion and flank the second slot. The top ridge and the bottom ridge may be positioned opposite to each other and adapted to provide torsional stability for PLIF insertion of the lateral member into the vertebral body. The top contour surface and the bottom contour surface may be dimensioned and configured to accommodate an angled anatomy of a vertebral endplate.

In addition, the lateral member further includes a cavity, a plurality of holes and a plurality of pins. The cavity is configured through the top wall and the bottom wall and comprises a plurality of ribs. The plurality of ribs may be positioned parallel to each other and may be adapted to provide structural integrity to the lateral member. The plurality of holes and the plurality of pins are positioned on the second lateral portion such that each hole is positioned on opposite diagonal corners of the second lateral portion, and each pin is positioned on opposite diagonal corners of the second lateral portion. The plurality of pins may be composed of materials capable of detection by x-ray imaging. The lateral member may further comprise a concave edge positioned opposite to the first slot. The concave edge may be adapted to form a funnel when aligned with a concave edge of a complementary lateral member. The first slot and the second slot may be dimensioned and configured to permit medial bone growth on the lateral member, and the plurality of cuts may be dimensioned and configured to permit lateral bone growth in the lateral member.

In yet another aspect, a modular lateral expansion device to structurally support a vertebral body comprises a pair of members. Each of the lateral members includes a first end, a second end, a first lateral portion, a second lateral portion, a top wall, and a bottom wall. The first end includes a curved configuration. The second end includes a substantially flat configuration and is positioned opposite to the first end. The first lateral portion and the second lateral portion are attached to each of the first end and the second end. The second lateral portion is positioned opposite to the first lateral portion. The top wall and the bottom wall are attached to each of the first end, the second end, and the pair of lateral portions. The bottom wall is positioned opposite to the top wall.

The second end further comprises a hole dimensioned and configured to permit insertion means to grip and remove the apparatus into the vertebral body. The first lateral portion includes a plurality of cuts. The plurality of cuts may be dimensioned and configured to permit lateral bone growth in the lateral member. The second lateral portion includes a first slot positioned at an edge of the second lateral portion and a second slot positioned in a substantially central area of the second lateral portion. The first slot and the second slot may be dimensioned and configured to permit medial bone growth on the lateral member. The top wall includes a top ridge and a top contour surface and the bottom wall includes a bottom ridge and a bottom contour surface. The top ridge and the bottom ridge are inwardly angled into the second lateral portion and flank the second slot. The top ridge and the bottom ridge may be positioned opposite to each other and adapted to provide torsional stability for PLIF insertion of the lateral member into a vertebral body. The top contour surface and the bottom contour surface may be dimensioned and configured to accommodate an angled anatomy of a vertebral endplate.

In addition, the lateral member further includes a cavity configured through the top wall and the bottom wall. The cavity further includes a plurality of ribs. The plurality of ribs may be positioned parallel to each other and may be adapted to provide structural integrity to the lateral member. A plurality of holes and a plurality of pins are positioned on the second lateral portion such that each hole is positioned on opposite diagonal corners of the second lateral portion, and each pin is positioned on opposite diagonal corners of the second lateral portion. A concave edge is positioned opposite to the first slot and adapted to form a funnel when aligned with a concave edge of a complementary lateral member. The plurality of pins is composed of materials capable of detection by x-ray imaging. The materials may comprise any of titanium and tantalum.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new modular lateral expansion device for placing between vertebral bodies within the vertebral body both in lateral and cephalocaudal directions for enhanced structural support of the spine. The embodiments herein achieve this by providing a modular lateral expansion device to be inserted into a vertebral body, the modular lateral expansion device comprising a pair of complementary lateral members. Each lateral member includes a first end, a second end positioned opposite to the first end, a first lateral portion, a second lateral portion, a top wall, and a bottom wall. The first lateral portion and the second lateral portion are positioned opposite to each other and are attached to each of the first end and the second end. The top wall and the bottom wall are attached to each of the first end, the second end, the first lateral portion, and the second lateral portion. The bottom wall is positioned opposite to the top wall. The second end further includes a hole. The first lateral portion further includes a plurality of cuts. The second lateral portion further includes a first slot positioned at an edge of the second lateral portion and a second slot positioned in a substantially central area of the second lateral portion. The top wall includes a top ridge and a top contour surface and the bottom wall further includes a bottom ridge and a bottom contour surface. The top ridge and the bottom ridge are inwardly angled into the second lateral portion and flank the second slot. The lateral member further includes a cavity configured through the top wall and the bottom wall. The cavity further includes a plurality of ribs. Referring now to the drawings, and more particularly to FIGS. 1A through 2C, where similar reference characters denote corresponding features consistently throughout the figures, there are shown preferred embodiments.

FIGS. 1A through 1F illustrate various perspective views of a lateral member 100 of a modular lateral expansion device (of FIGS. 2A through 2C) according to an embodiment herein. The lateral member 100 includes a first end 102, a second end 104, a first curved lateral portion 106, a second flattened lateral portion 108, a top wall 110, and a bottom wall 134. The second end 104 is positioned opposite to the first end 102. The first lateral portion 106 and the second lateral portion 108 are positioned opposite to each other and are attached to each of the first end 102 and the second end 104. The top wall 110 and the bottom wall 134 are attached to each of the first end 102, the second end 104, the first lateral portion 106, and the second lateral portion 108. The bottom wall 134 is positioned opposite to the top wall 110.

The second end 104 further includes a hole 112. The first lateral portion 106 further includes three cuts 140, 142, 144 positioned adjacent to each other and a recess 146. The recess 146 is connected to the cut 144. The three cuts 140, 142, 144 are of uniform length and width. The second lateral portion 108 further includes a first slot 114, a second slot 116, a plurality of holes 118, 120, a plurality of pins 122, 124, and a concave edge 126. The first slot 114 is positioned at an edge of the second lateral portion 108. The second slot 116 is positioned in a substantially central area of the second lateral portion 108. The holes 118, 120 and the pins 122, 124 are located at four opposite corners of the second lateral portion 108. Preferably, the holes 118, 120 are positioned diagonally opposite to one another and the pins 122, 124 are positioned diagonally opposite to one another. The first slot 114 is located between the hole 118 and the pin 122. The concave edge 126 is located opposite to the first slot 114 and may be adapted to form a funnel (when aligned with a concave edge of a complementary lateral member lateral member 100a as shown in FIG. 2A through 2C).

In addition, the lateral member 100 further includes a cavity 128 configured through the top wall 110 and the bottom wall 134. The length of the cavity 128 is at least equal to half of an overall length of the lateral member 100. The top wall 110 further includes a top ridge 130 and a top contour surface 132. The bottom wall 134 further comprises a bottom ridge 136 and a bottom contour surface 138. The top ridge 130 and the top contour surface 132 are located opposite to the bottom ridge 136 and the bottom contour surface 138. The top ridge 130 and the bottom ridge 136 are inwardly angled into the second lateral portion 108 and flank the second slot 116. Additionally, the cavity 128 further comprises a plurality of ribs 148, 150 located parallel to each other and in between the first lateral portion 106 and the second lateral portion 108.

Figure 1A:
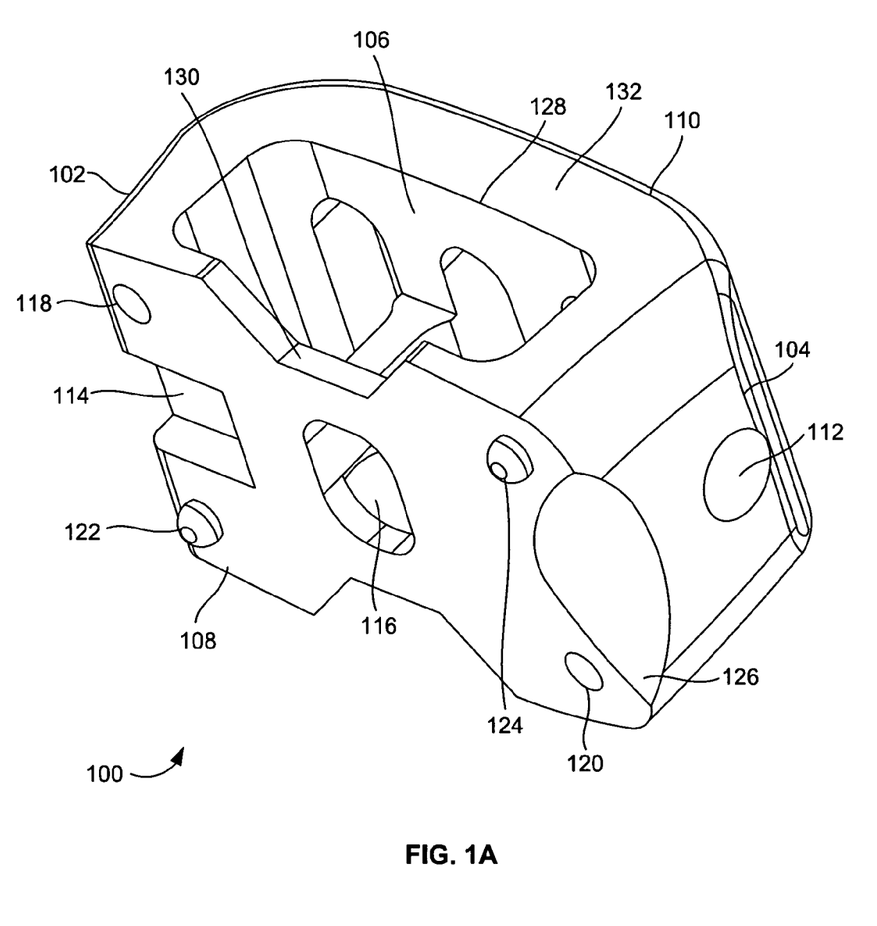
FIGS. 1A through 1F illustrate various perspective views of a lateral member of a modular lateral expansion device according to an embodiment herein.
Figure 1B:
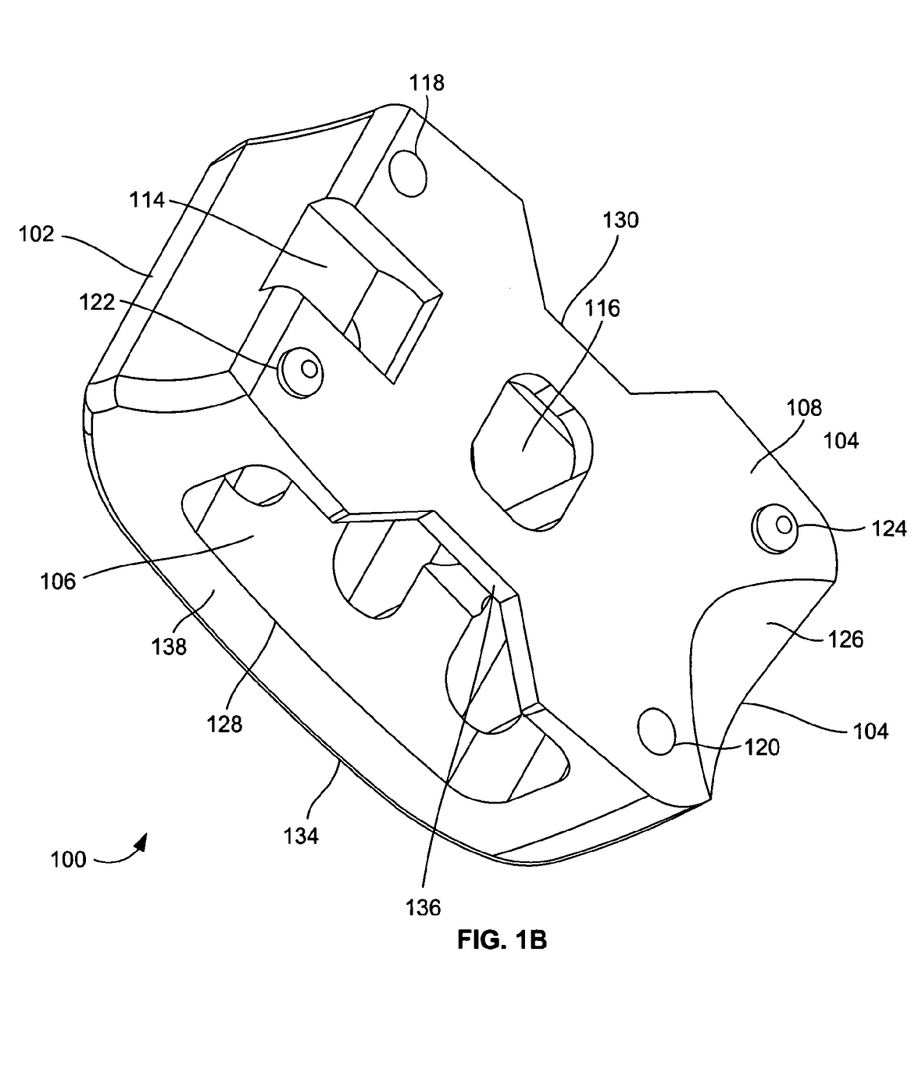
Figure 1C:
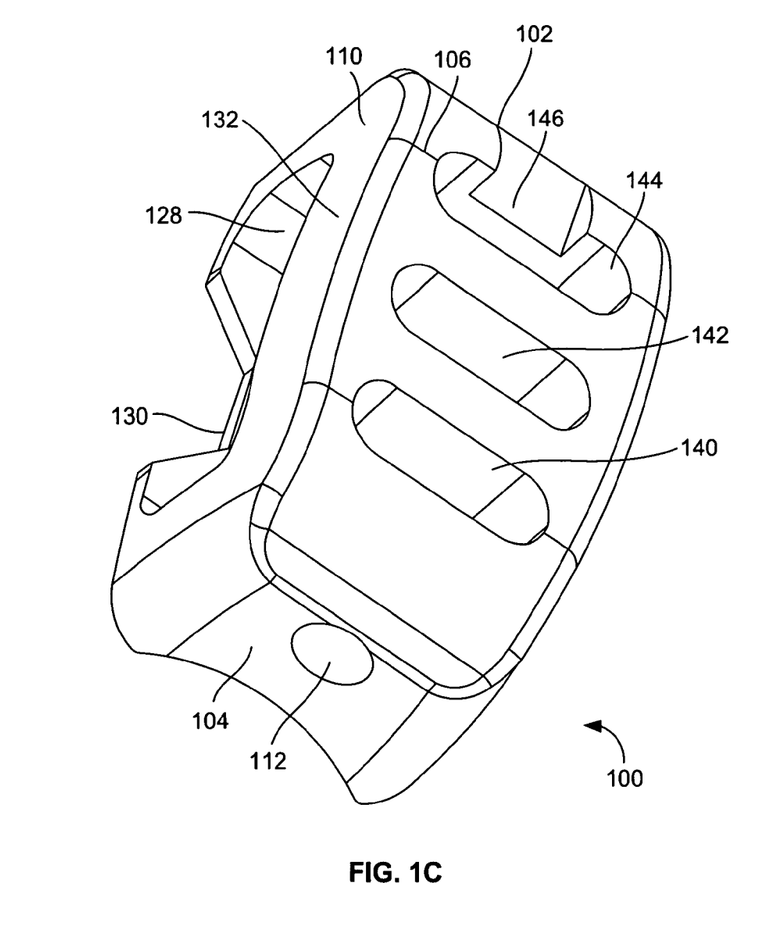
Figure 1D:
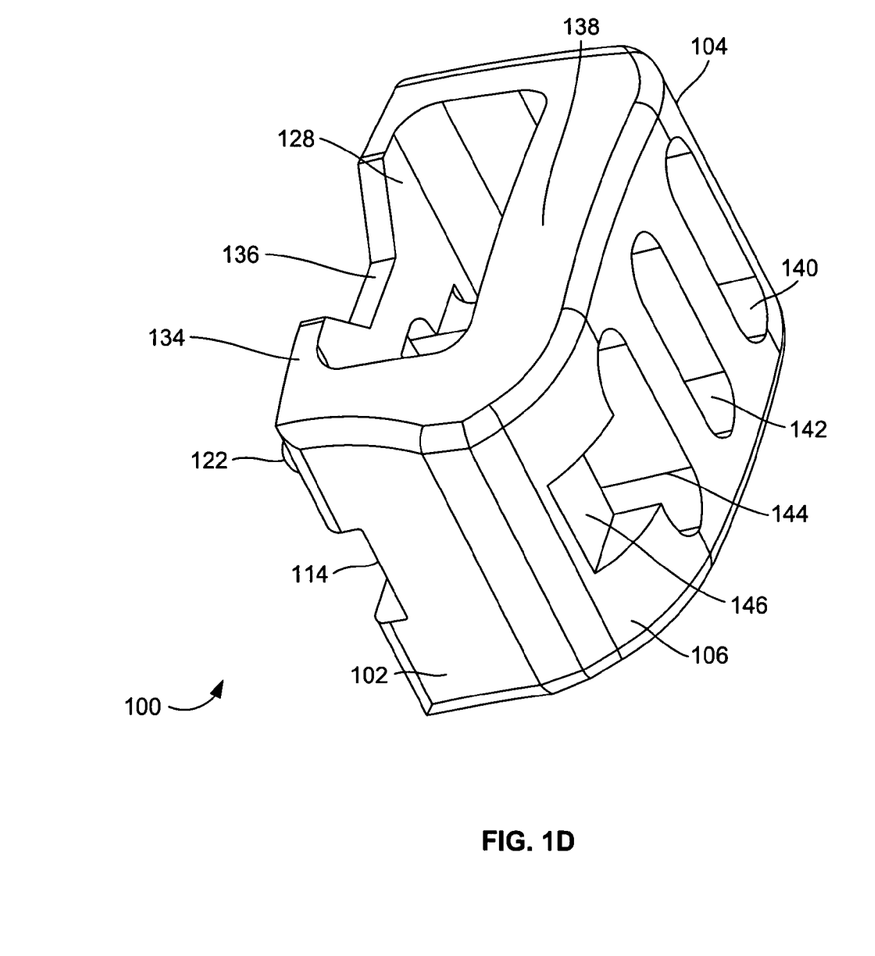
Figure 1E:
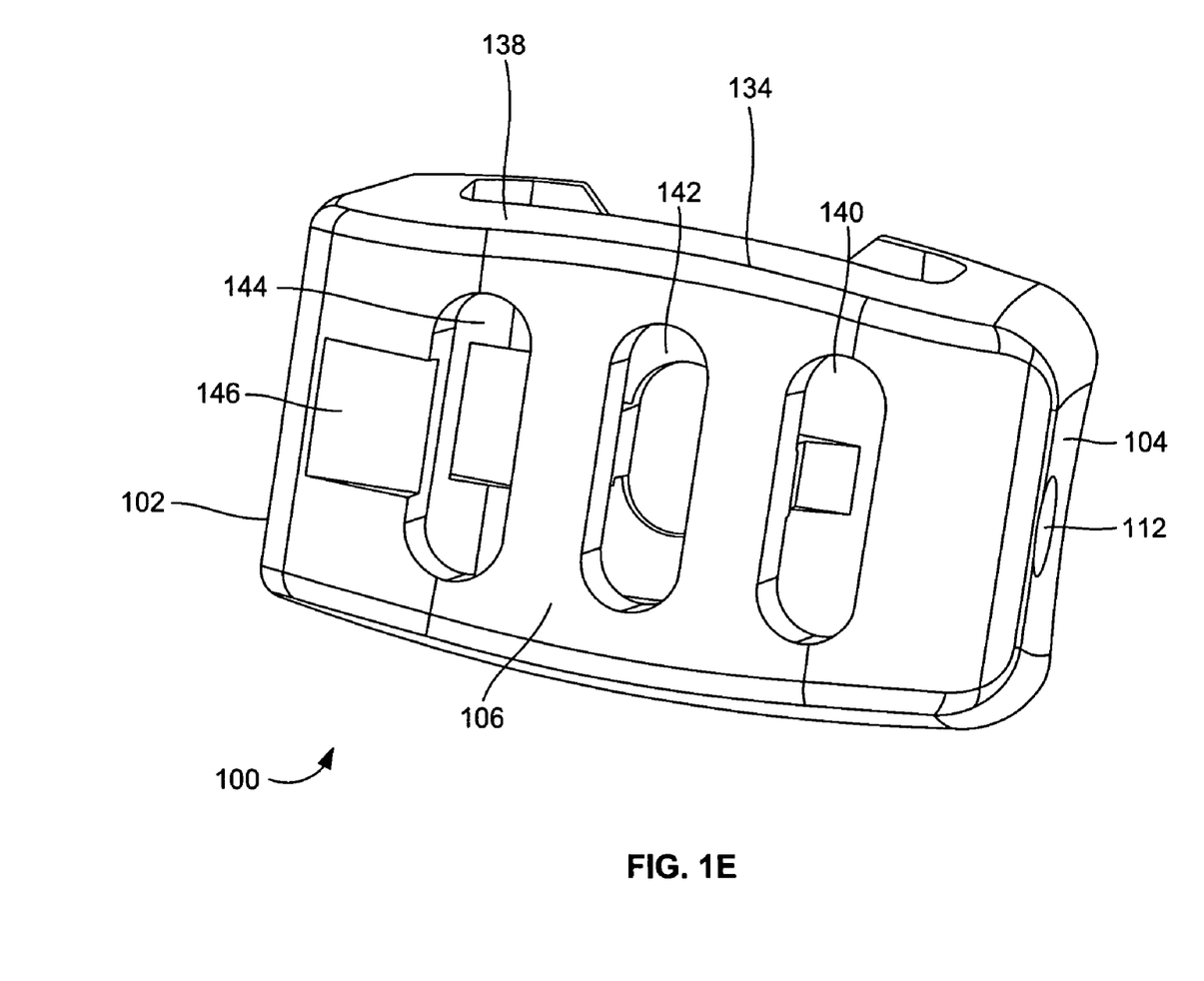
Figure 1F:
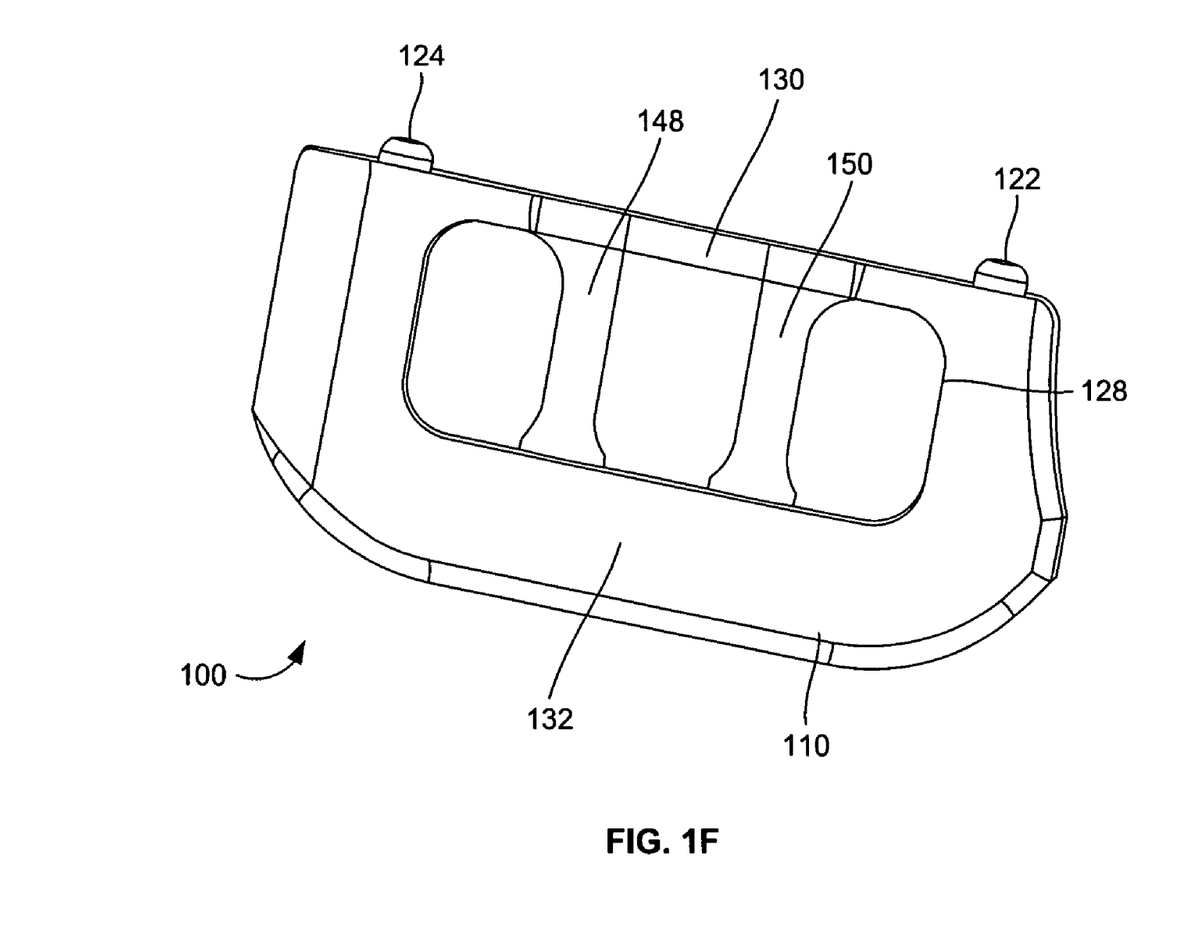
Figure 2A:
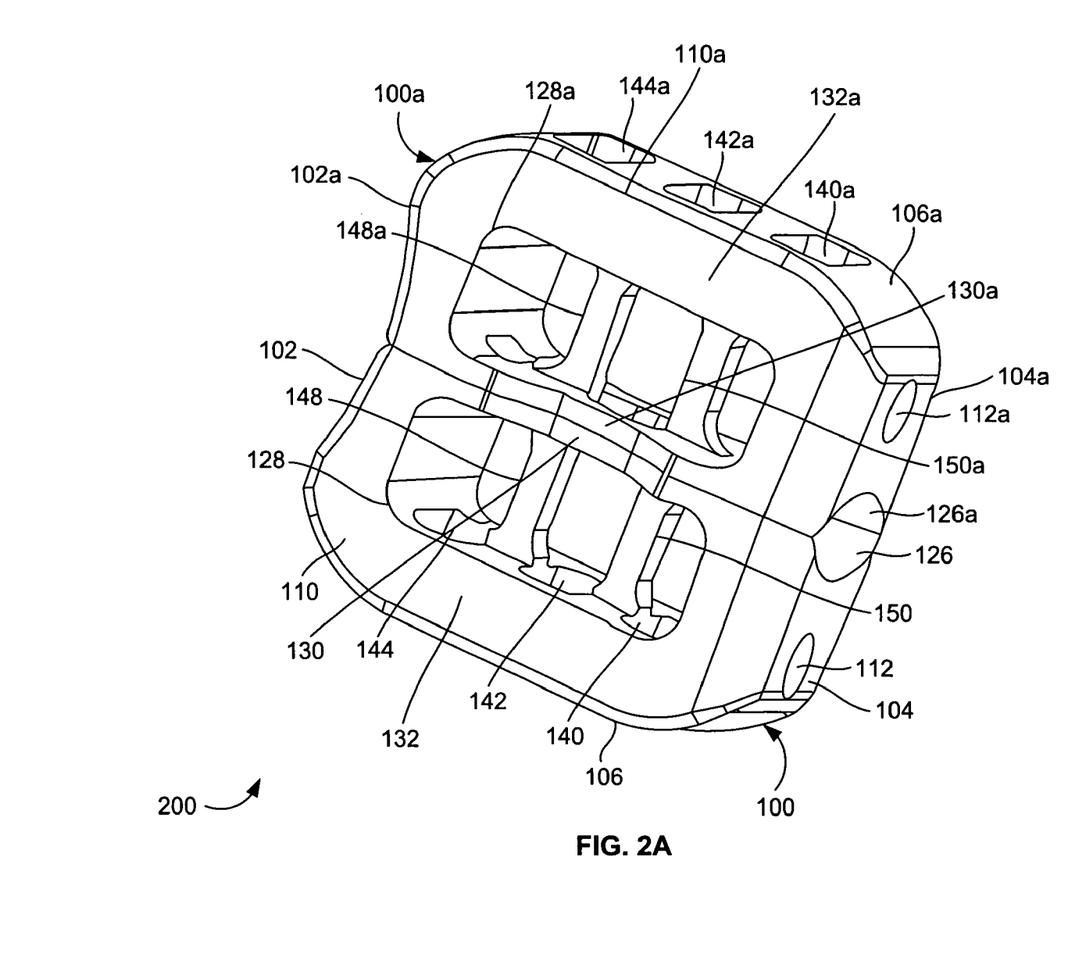
FIGS. 2A through 2C illustrate perspective views of a modular lateral expansion device having a pair of lateral members shown in an anterior position, a posterior position, and a lateral position, respectively, according to an embodiment herein.
Figure 2B:
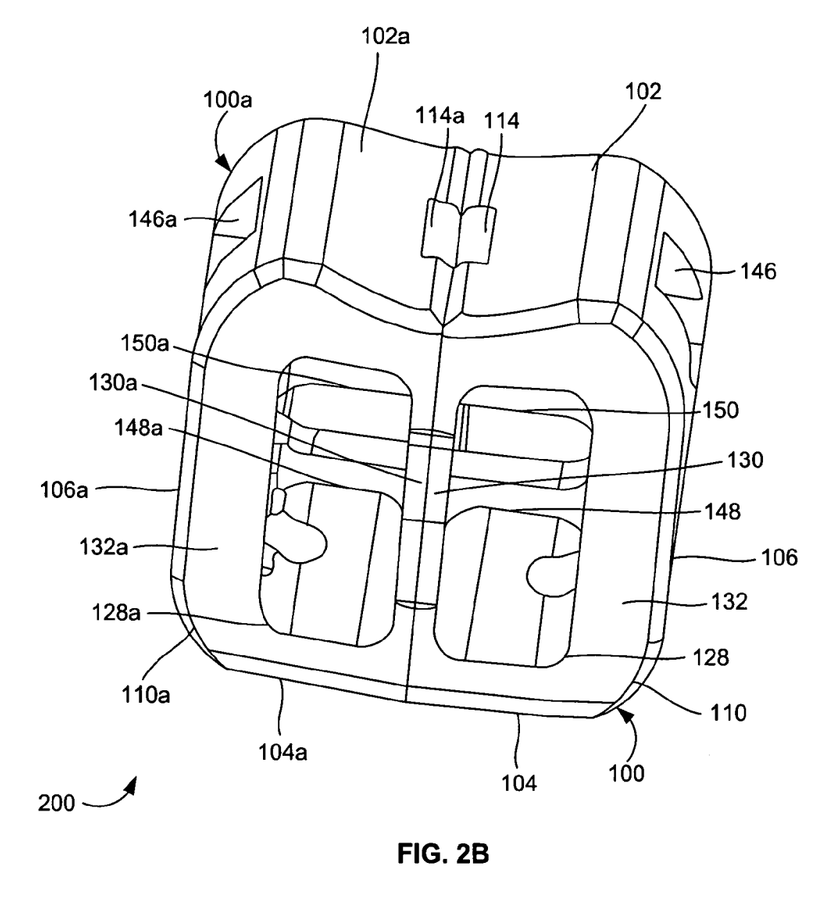
Figure 2C:
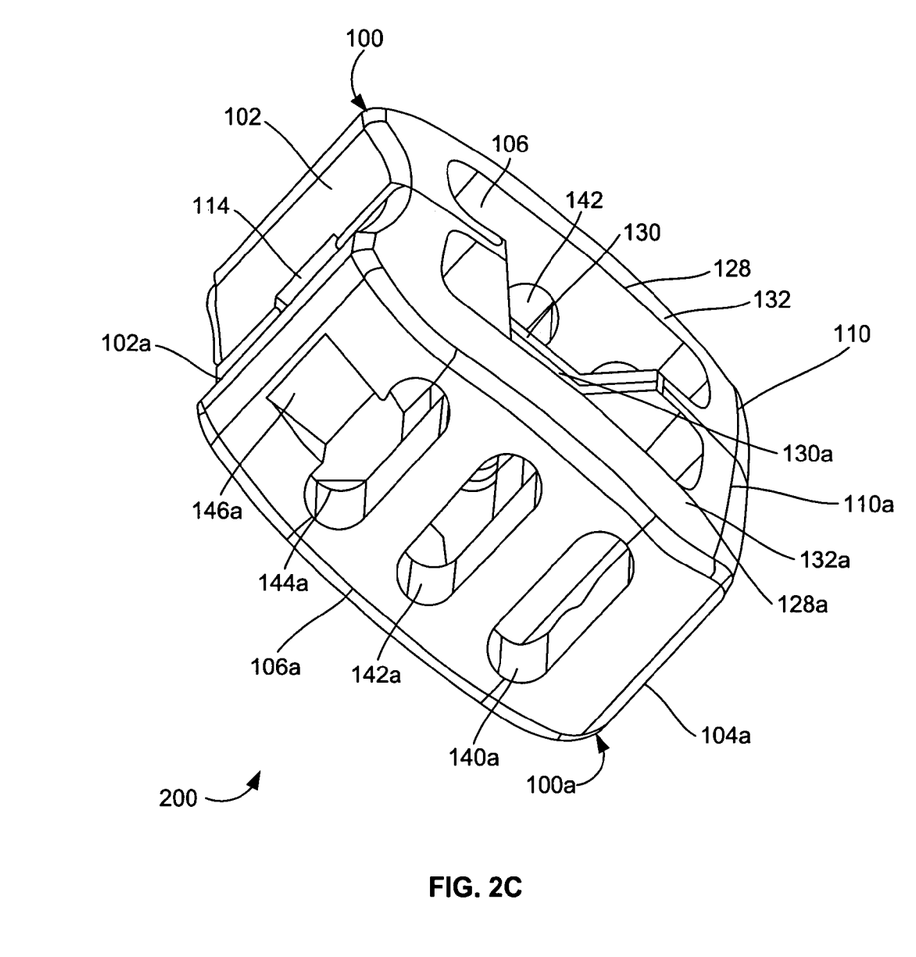

FIGS. 2A through 2C illustrate perspective views of a modular lateral expansion device 200 having a pair of lateral members 100, 100a shown in an anterior position, a posterior position, and a lateral position, respectively, according to an embodiment herein. In FIGS. 2A through 2C, the modular lateral expansion device 200 is shown in a non-extended position. The lateral member 100, 100a may each form one complementary component of the implant (e.g., a modular lateral expansion device 200 of FIG.2A through 2C). The first slot 114 and the second slot 116 are dimensioned and configured to permit medial bone growth in the lateral member 100, 100a. The lateral member 100 is attached to the lateral member 100a. Specifically, the holes 118, 120 of the lateral member 100 mate with the corresponding pins 122, 124 of the other lateral member 100a and keep the implant aligned during interbody fusion insertion (e.g., anterior lumbar interbody fusion (ALIF) surgical technique).

The pins 122, 124 preferably comprise either titanium or tantalum and are adapted for x-ray positioning. That is, once the device 200 is inserted into the vertebral body, an x-ray of the area may be taken to reveal the relative positions of the pins 122, 124. Because the pins 122, 124 are composed of titanium or tantalum and are not radiolucent, they would show up on the x-ray imaging. If the pins 122, 124 are not properly aligned (as detected by the x-ray imaging), then the device 200 may be re-positioned by the surgeon without having to remove the device 200. The concave edge 126, 126a are joined to each other to form a funnel shape. The top ridges 130, 130a remain aligned to each other at the same planar level. The ribs 148, 148a are aligned to another and are positioned parallel to ribs 150, 150a (which are also aligned to one another), respectively.

The modular lateral expansion device 200 is placed in a vertebral body (not shown) having an outer portion (e.g., the outer 30% of a cortical tissue of the vertebral body). The top contour surfaces 132, 132a and the bottom contour surface 138 (not shown in FIGS. 2A through 2C) may be adapted to connect with a vertebral endplate (not shown). The contour surfaces 132, 132a, 138 are dimensioned and configured (i.e., convex shape with an appropriate taper to match the geometry of an endplate (not shown)) to accommodate an angled anatomy of the vertebral end plate and to achieve kyphosis (e.g., a curvature of the upper spine) or lordosis (e.g., an inward curvature of a portion of the vertebral column).

The cavities 128, 128a are adapted for bone packing before insertion and the funnel formed by the concave edges 126, 126a are adapted for bone packing after insertion. The slots 114, 114a and the slot 116 (not shown in FIGS. 2A through 2C) are dimensioned and configured to permit bone packing to allow medial bone growth and lateral bone growth, which may be allowed through the cuts 140, 140a, 142, 142a, 144, 144a. The ribs 148, 148a, 150, 150a are dimensioned and configured to provide structural integrity to the modular lateral expansion device 200.

The modular lateral expansion device 200 can be used for both ALIF and PLIF surgeries. The holes 112, 112a allow for gripping and removal of the modular lateral expansion device 200 into the intervertebral space during ALIF surgeries by allowing an inserter tool (not shown), which may be any suitable type of inserter tool, to be inserted into the holes 112, 112a. The holes 118 and 120 of the lateral member 100 mate with the pins 122, 124 of the lateral member 100a and keep the modular lateral expansion device 200 aligned during ALIF insertion. For PLIF insertion, the recesses 146, 146a and the slot 114, 114a may be adapted for bone graft insertion.

The top ridges 130, 130a and the bottom ridge 136 (not shown in FIGS. 2A through 2C) are adapted to provide torsional stability to PLIF insertion of the lateral member 100 into the vertebral body. The modular lateral expansion device 200 can be placed both in the lateral and cephalocaudal directions within the vertebral body and the position of the modular lateral expansion device 200 can be maintained because when the device 200 is impacted in between two vertebral endplates (not shown), it is separated either through a built-in separator mechanism (not shown) or through a separate tool (not shown) and is under constant pressure to restore the original height of the disc space.

In one embodiment, the modular lateral expansion device 200 is constructed using materials such as PEEK™ (Polyetheretherketon) plastic available from Whitford Worldwide Company, Delaware, USA, titanium alloy, and carbon fiber. Moreover, the modular lateral expansion device 200 has the capacity to reproducibly separate in situ (e.g., in the original position) in the sagittal plane (e.g., a plane that divides the body of a bilaterally symmetrical animal into right and left portions). Once the modular lateral expansion device 200 is placed within the outer portion of the vertebral body, it can distract and the lateral member 100 can be separated and laterally displaced with respect to the lateral member 100a. Further bone grafting may be allowed by filling the cavities 128, 128a with bone grafting material which allows for greater fusion surface area.

Additionally, the modular lateral expansion device 200 can be distracted bidirectionally both in the lateral and cephalocaudal directions in situ. The device 200 also solves the problems of subsidence and poor placement by allowing for lateral reproducible placement of the lateral members 100, 100a. During direct central placement with the vertebral endplate (not shown), the top ridges 130, 130a of the modular lateral expansion device 200 accommodate the vertebral endplate, thereby not requiring a cutting device and decreasing risk of implant failure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A modular lateral expansion device to be inserted into a vertebral body, said modular lateral expansion device comprising a pair of complementary lateral members, wherein each lateral member comprises:
    a first end portion;
    a second end portion positioned opposite to said first end portion and having a hole;
    a first lateral portion attached to each of said first end portion and said second end portion and having a plurality of cuts;
    a second lateral portion positioned opposite to said first lateral portion and attached to each of said first end portion and said second end portion and having a first slot positioned at an edge of said second lateral portion and a second slot positioned in a substantially central area of said second lateral portion;
    a top wall attached to each of said first end portion, said second end portion, and said pair of lateral portions and having a top ridge and a top contour surface, wherein said top ridge is inwardly angled to form a first outwardly facing trapezoidal cutout shape into said second lateral portion;
    a bottom wall positioned opposite to said top wall and attached to each of said first end portion, said second end portion, and said pair of lateral portions and having a bottom ridge and a bottom contour surface, wherein said bottom ridge is inwardly angled to form a second outwardly facing trapezoidal cutout shape into said second lateral portion, and wherein said top ridge and said bottom ridge flank said second slot; and
    a cavity configured through said top wall and said bottom wall and having a plurality of ribs, wherein said ribs are positioned opposite to said first slot and said second slot;
    wherein said lateral member further comprises a plurality of holes and a plurality of pins positioned on said second lateral portion such that each hole is positioned on opposite diagonal corners of said second lateral portion, and each pin is positioned on opposite diagonal corners of said second lateral portion.

2. The modular lateral expansion device of claim 1, wherein said plurality of ribs are positioned parallel to each other and are adapted to provide structural integrity to said lateral member.

3. The modular lateral expansion device of claim 1, wherein said plurality of pins are composed of materials capable of detection by x-ray imaging.

4. The modular lateral expansion device of claim 1, wherein said lateral member further comprises a concave edge positioned opposite to said first slot, said concave edge adapted to form a funnel when aligned with a concave edge of a complementary lateral member.

5. The modular lateral expansion device of claim 1, wherein said first slot and said second slot are dimensioned and configured to permit medial bone growth on said lateral member, and said plurality of cuts are dimensioned and configured to permit lateral bone growth in said lateral member.

6. The modular lateral expansion device of claim 1, wherein said top ridge and said bottom ridge are positioned opposite to each other and adapted to provide torsional stability for posterior lumbar interbody fusion (PLIF) insertion of said lateral member into a vertebral body.

7. The modular lateral expansion device of claim 3, wherein said materials comprise any of titanium and tantalum.

8. An apparatus to structurally support a vertebral body, wherein said apparatus comprises a pair of lateral members, and wherein each said lateral member comprises:
    a first end portion having a curved configuration;
    a second end portion having a substantially straight configuration and positioned opposite to said first end portion and, wherein said second end portion comprises a hole dimensioned and configured to permit insertion means to grip and remove said apparatus into said vertebral body;
    a first lateral portion attached to each of said first end portion and said second end portion and having a plurality of cuts;
    a second lateral portion positioned opposite to said first lateral portion and attached to each of said first end portion and said second end portion and having a first slot positioned at an edge of said second lateral portion and a second slot positioned in a substantially central area of said second lateral portion;
    a top wall attached to each of said first end portion, said second end portion, and said pair of lateral portions and having a top ridge and a top contour surface, wherein said top ridge is inwardly angled to form a first outwardly facing trapezoidal cutout shape into said second lateral portion;
    a bottom wall positioned opposite to said top wall and attached to each of said first end portion, said second end portion, and said pair of lateral portions and having a bottom ridge and a bottom contour surface, wherein said bottom ridge is inwardly angled to form a second outwardly facing trapezoidal cutout shape into said second lateral portion, and wherein said top ridge and said bottom ridge flank said second slot;

a cavity configured through said top wall and said bottom wall and having a plurality of ribs, wherein said ribs are positioned opposite to said first slot and said second slot; and a plurality of holes and a plurality of pins positioned on said second lateral portion such that each hole is positioned on opposite diagonal corners of said second lateral portion, and each pin is positioned on opposite diagonal corners of said second lateral portion, wherein said top ridge and said bottom ridge are positioned opposite to each other and adapted to provide torsional stability for posterior lumbar interbody fusion (PLIF) insertion of said lateral member into said vertebral body.

9. The apparatus of claim 8, wherein said plurality of ribs are positioned parallel to each other and are adapted to provide structural integrity to said lateral member.

10. The apparatus of claim 8, wherein said plurality of pins are composed of materials capable of detection by x-ray imaging.

11. The apparatus of claim 8, wherein said lateral member further comprises a concave edge positioned opposite to said first slot, said concave edge adapted to form a funnel when aligned with a concave edge of a complementary lateral member.

12. The apparatus of claim 8, wherein said first slot and said second slot are dimensioned and configured to permit medial bone growth on said lateral member, and said plurality of cuts are dimensioned and configured to permit lateral bone growth in said lateral member.

13. The apparatus of claim 8, wherein said top contour surface and said bottom contour surface are dimensioned and configured to accommodate an angled anatomy of a vertebral endplate.

14. A modular lateral expansion device to structurally support a vertebral body, wherein said modular lateral expansion device comprises a pair of members, wherein each said member comprises:

a first end portion having a curved configuration;

a second end portion having a substantially flat configuration and positioned opposite to said first end portion and, wherein said second end portion comprises a hole dimensioned and configured to permit insertion means to grip and remove said apparatus into said vertebral body;

a first lateral portion attached to each of said first end portion and said second end portion and having a plurality of cuts;

a second lateral portion positioned opposite to said first lateral portion and attached to each of said first end portion and said second end portion and having a first slot positioned at an edge of said second lateral portion and a second slot positioned in a substantially central area of said second lateral portion;

a top wall attached to each of said first end portion, said second end portion, and said pair of lateral portions and having a top ridge and a top contour surface, wherein said top ridge is inwardly angled to form a first outwardly facing trapezoidal cutout shape into said second lateral portion;

a bottom wall positioned opposite to said top wall and attached to each of said first end portion, said second end portion and said pair of lateral portions and having a bottom ridge and a bottom contour surface, wherein said bottom ridge is inwardly angled to form a second outwardly facing trapezoidal cutout shape into said second lateral portion, and wherein said top ridge and said bottom ridge flank said second slot;

a cavity configured through said top wall and said bottom wall and having a plurality of ribs, wherein said ribs are positioned opposite to said first slot and said second slot;

a plurality of holes and a plurality of pins positioned on said second lateral portion such that each hole is positioned on opposite diagonal corners of said second lateral portion, and each pin is positioned on opposite diagonal corners of said second lateral portion; and a concave edge positioned opposite to said first slot, said concave edge adapted to form a funnel when aligned with a concave edge of a complementary lateral member, wherein said plurality of pins are composed of materials capable of detection by x-ray imaging.

15. The modular lateral expansion device of claim 14, wherein said plurality of ribs are positioned parallel to each other and are adapted to provide structural integrity to said lateral member.

16. The modular lateral expansion device of claim 14, wherein said first slot and said second slot are dimensioned and configured to permit medial bone growth on said lateral member, and said plurality of cuts are dimensioned and configured to permit lateral bone growth in said lateral member.

17. The modular lateral expansion device of claim 14, wherein said top ridge and said bottom ridge are positioned opposite to each other and adapted to provide torsional stability for posterior lumbar interbody fusion (PLIF) insertion of said lateral member into a vertebral body.

18. The modular lateral expansion device of claim 14, wherein said materials comprise any of titanium and tantalum.

19. The modular lateral expansion device of claim 14, wherein said top contour surface and said bottom contour surface are dimensioned and configured to accommodate an angled anatomy of a vertebral endplate.

* * * * *